United States Patent

Picard et al.

[11] Patent Number: 5,254,589
[45] Date of Patent: Oct. 19, 1993

[54] SULFONYL UREA AND CARBAMATE ACAT INHIBITORS

[75] Inventors: Joseph A. Picard, Ypsilanti; William H. Roark; Bruce D. Roth, both of Ann Arbor, all of Mich.

[73] Assignee: Warner-Lambert Company, Morris Plains, N.J.

[21] Appl. No.: 776,112

[22] Filed: Oct. 15, 1991

[51] Int. Cl.$^5$ .................................. A61K 31/175
[52] U.S. Cl. .................. 514/592; 514/520; 514/529; 514/562
[58] Field of Search ............ 514/592, 593, 522, 532, 514/534, 538, 540, 520, 562, 564, 568; 564/39, 42; 558/417; 560/103, 110; 562/433

[56] References Cited

U.S. PATENT DOCUMENTS

| | | | |
|---|---|---|---|
| 2,975,212 | 3/1961 | Wagner et al. | 564/39 |
| 4,013,706 | 3/1977 | Anatol et al. | 564/39 |
| 4,845,128 | 7/1989 | Harper et al. | 514/592 |

FOREIGN PATENT DOCUMENTS

| | | | |
|---|---|---|---|
| 613312 | 1/1961 | Canada | 564/39 |
| 1034618 | 7/1958 | Fed. Rep. of Germany | 564/39 |
| 2501681 | 7/1981 | France | 153/9 |
| 407978 | 9/1966 | Switzerland. | |

*Primary Examiner*—Allen J. Robinson
*Assistant Examiner*—Shailendra Kumar
*Attorney, Agent, or Firm*—Ruth H. Newtson; Michael J. Atkins

[57] ABSTRACT

A pharmaceutically useful compound which lowers blood cholesterol levels having the formula

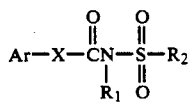

wherein X is oxygen or —NH—; Ar is phenyl, substituted phenyl, naphthyl or substituted naphthyl; $R_1$ is hydrogen, lower alkyl or benzyl; and $R_2$ is a straight or branched alkyl group having from 5 to 17 carbon atoms which may be substituted on the 1-carbon position with methyl, ethyl, phenyl, or substituted phenyl, or a cycloalkyl group having from 3 to 8 carbon atoms.

3 Claims, No Drawings

SULFONYL UREA AND CARBAMATE ACAT INHIBITORS

BACKGROUND OF THE INVENTION

The present invention describes a series of novel sulfonyl ureas and carbamates which inhibit acyl-CoA:-cholesterol acyltransferase (ACAT), the enzyme responsible for the esterification of dietary cholesterol. Such agents may decrease the absorption of dietary cholesterol and therefore provide a therapy for individuals with hypercholesterolemia.

INFORMATION DISCLOSURE STATEMENT

Swiss Patent 407,978 (Chem. Pharm. Fabrik.), published Sep. 30, 1966 (Derwent 24231), describes compounds of the following formula as hypoglycemic agents:

$RSO_2NHCONHR$ wherein R is alkyl, cycloalkyl, alkylcycloalkyl optionally substituted by one or more halogen or CNS groups or alkyl substituted phenyl in which at least one of the substituents is halogen or CNS groups and the alkyl group contains 3 to 8 carbon atoms.

The following specific compounds are disclosed:

$C_4H_9-NHCONHSO_2(CH_2)_3CH_2Cl$;

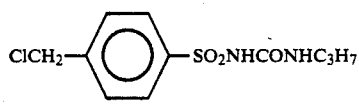

and

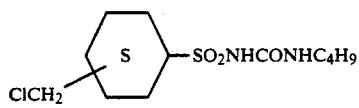

French Patent 2,501, 681 (Ciba-Geigy), published Jul. 15, 1981, describes the following compounds as agrochemical bioregulators (microbicides, bactericides, and fungicides):

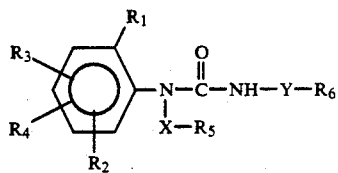

wherein $R_1$ is alkyl$C_{1-4}$, alkoxy$C_{1-4}$, or halogen; $R_2$ is hydrogen, alkyl$C_{1-3}$, alkoxy$C_{1-4}$, or halogen; $R_3$ is hydrogen, alkyl$C_{1-3}$, or halogen; $R_4$ is hydrogen or methyl; provided the total number of carbons in the $R_1$, $R_2$, $R_3$, and $R_4$ substituents does not total more than 8;

X is —CH$_2$— or

$R_5$ is —COOR', COSR', or

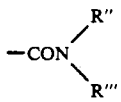

wherein R',
R", R''' are independently methyl or ethyl;
Y is

—SO$_2$—; and $R^6$ is
(a) alkyl$C_{1-6}$ optionally substituted with halogen or alkoxy$C_{1-3}$; or alkenyl $C_{2-6}$ optionally substituted with halogen; or alkynyl$C_{3-6}$ or cycloalkyl $C_{3-6}$;
(b) phenyl or benzyl optionally substituted with halogen, nitro, alkyl$C_{1-3}$, or alkoxy$C_{1-3}$; or
(c) a 5- or 6-member heterocyclic which is saturated, unsaturated, or partially saturated optionally substituted with alkyl$C_{1-3}$, or halogen and contains at least one oxygen atom.

The compounds of this reference which are most closely related structurally to the present invention are the following:

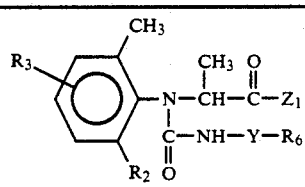

| $R_2$ | $R_3$ | $Z_1$ | $Y-R_6$ |
|---|---|---|---|
| $CH_3$ | 3-$CH_3$ | —$OCH_3$ | —$SO_2CH_3$ |
| —Cl | H | —$OCH_3$ | —$SO_2CH_3$ |
| —Cl | H | —$OCH_3$ | —$SO_2$-C$_6$H$_4$-$CH_3$ |
| —$CH_3$ | 3-$CH_3$ | —$OC_2H_5$ | —$SO_2CH_3$ |
| —$CH_3$ | 3-$CH_3$ | —$OCH_3$ | —$SO_2$-C$_6$H$_5$ |
| —$C_2H_5$ | H | —$SCH_3$ | —$SO_2CH_2CH_2Cl$ |
| —$CH_3$ | 3-$CH_3$ | —$OCH_3$ | —$SO_2$-C$_6$H$_4$-Cl |
| —$CH_3$ | H | —$OCH_3$ | —$SO_2CH_2CH_2Cl$ |
| —$CH_3$ | -3-Br | —$OCH_3$ | —$SO_2CH_3$ |
| —$C_2H_5$ | H | —$SCH_3$ | —$SO_2CHClCH_2Cl$ |
| —$C_2H_5$ | H | —$N(CH_3)_2$ | —$SO_2CH_3$ |
| —$C_2H_5$ | 4-Br | —$OCH_3$ | —$SO_2CH_3$ |
| —$CH_3$ | 4-Br | —$OCH_3$ | —$SO_2C_2H_5$ |
| —$C_2H_5$ | H | —$OCH_3$ | —$SO_2CH_3$ |
| —$C_2H_5$ | H | —$N(C_2H_5)_2$ | —$SO_2CH_3$ |

-continued

| | | | |
|---|---|---|---|
| —C₂H₅ | 4-Br | —OCH₃ | —SO₂—⟨C₆H₄⟩—CH₃ |
| —C₂H₅ | H | —OCH₃ | —SO₂C₂H₅ |
| —C₂H₅ | H | —OCH₃ | —SO₂—⟨C₆H₅⟩ |
| —C₂H₅ | H | —OCH₃ | —SO₂—⟨C₆H₄⟩—Cl |
| —C₂H₅ | H | —N(CH₃)₂ | —SO₂C₂H₅ |
| —C₂H₅ | H | —OCH₃ | —SO₂—⟨C₆H₄⟩—CH₃ |
| —CH₃ | H | —OCH₃ | —SO₂CHClCH₂Cl |
| —CH₃ | H | —OCH₃ | —SO₂CH₃ |
| —CH₃ | H | —OCH₃ | —SO₂C₂H₅ |
| —CH₃ | H | —OCH₃ | —SO₂—⟨C₆H₅⟩ |
| —CH₃ | H | —OCH₃ | —SO₂—⟨C₆H₄⟩—Cl |
| —CH₃ | H | —OCH₃ | —SO₂—⟨C₆H₄⟩—CH₃ |
| —CH₃ | 4-CH₃ | —OCH₃ | —SO₂C₂H₅ |
| —CH₃ | 4-CH₃ | —OCH₃ | —SO₂—⟨C₆H₄⟩—CH₃ |
| —C₂H₅ | H | —OCH₃ | —SO₂CHClCH₂Cl |
| —CH₃ | H | —SCH₃ | —SO₂—⟨C₆H₄⟩—CH₃ |

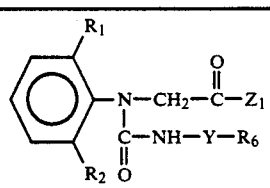

| R₁ | R₂ | Z₁ | Y—R₆ |
|---|---|---|---|
| C₂H₅ | C₂H₅ | —N(CH₃)₂ | —SO₂C₂H₅ |
| t-C₄H₉ | H | —N(CH₃)₂ | —SO₂CH₃ |
| CH₃ | —OCH₃ | —N(C₂H₅)₂ | —SO₂CH₃ |
| i-OC₃H₇ | H | —N(CH₃)₂ | —SO₂CH₃ |
| Cl | Cl | —N(CH₃)₂ | —SO₂CH₃ |
| CH₃ | C₂H₅ | —N(C₂H₅)₂ | —SO₂C₂H₅ |
| C₂H₅ | —C₂H₅ | —N(CH₃)₂ | —SO₂CH₂CH₂Cl |

-continued

| | | | |
|---|---|---|---|
| i-OC₃H₇ | H | —N(C₂H₅)₂ | —SO₂C₂H₅ |
| CH₃ | —OCH₃ | —N(C₂H₅)₂ | —SO₂C₂H₅ |
| Z—C₄H₉ | H | —N(C₂H₅)₂ | —SO₂C₂H₅ |
| CH₃ | —C₂H₅ | —N(C₂H₅)₂ | —SO₂CH₃ |

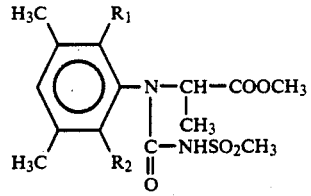

SUMMARY OF THE INVENTION

The present invention provides pharmaceutically useful compounds of the following general Formula I:

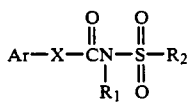

Formula I wherein X is oxygen or —NH—; wherein Ar is
(a) phenyl which is unsubstituted or is substituted with from one to three substituents selected from:
 alkyl having from 1 to 4 carbon atoms and which is straight or branched,
 alkoxy having from 1 to 3 carbon atoms and which is straight or branched,
 hydroxy,
 fluorine,
 chlorine,
 bromine,
 nitro,
 cyano,
 trifluoromethyl,
 —COOH,
 —COOalkyl wherein alkyl has from 1 to 4 carbon atoms and which is straight or branched,
 —(CH₂)$_m$NR₃R₄ wherein m is zero or one, and each of R₃ and R₄ is hydrogen or a straight or branched alkyl group having 1 to 4 carbon atoms;
(b) 1- or 2-naphthyl which is unsubstituted or substituted with one to three substituents selected from:
 alkyl having from 1 to 4 carbon atoms and which is straight or branched,
 alkoxy having from 1 to 3 carbon atoms and which is straight or branched,
 hydroxy,
 fluorine,
 chlorine,
 bromine,
 nitro,
 cyano,
 trifluoromethyl,
 —COOH,
 —COOalkyl wherein alkyl has from 1 to 4 carbon atoms and is straight or branched,
 —(CH₂)$_m$NR₃R₄ wherein m, R₃, and R₄ have the meanings defined above;
wherein R₁ is hydrogen, lower alkyl having from 1 to 4 carbon atoms or benzyl;
wherein R₂ is

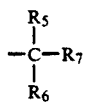

wherein each of $R_5$ and $R_6$ is hydrogen, methyl, ethyl, phenyl, phenyl substituted with straight or branched lower alkyl having from 1 to 4 carbon atoms, straight or branched lower alkoxy having from 1 to 4 carbon atoms, chlorine, fluorine or bromine, or $R_5$ and $R_6$ together with the carbon atom to which they are attached form a cyclic group having from 3 to 8 carbon atoms; and $R_7$ is a straight or branched alkyl group having from 4 to 16 carbon atoms; and pharmaceutically acceptable salts thereof.

The compounds of Formula I are useful in treating atherosclerosis.

DETAILED DESCRIPTION OF INVENTION

Pharmaceutically acceptable salts of the compounds of Formula I are also included as a part of the present invention.

The base salts may be generated from compounds of Formula I by reaction of an appropriate compound of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Stephen N. Berge, et al, J. Pharm. Sci. 66, 1–19 (1977).

Suitable acids for forming acid salts of the compounds of Formula I containing a basic group include, but are not necessarily limited to acetic, benzoic, benzenesulfonic, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

Certain compounds of the present invention may also exist in different stereoisomeric forms by virtue of the presence of asymmetric centers in the compound. The present invention contemplates all stereoisomers may be obtained, if desired, by methods known in the art as, for example, the separation of stereoisomers in chiral chromatographic columns.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

Illustrative examples of straight or branched alkyl groups having from 4 to 16 carbon atoms include n-butyl, iso-butyl, tert-butyl, n-pentyl, isopentyl, n-hexyl, n-heptyl, n-octyl, n-undecyl, n-dodecyl, n-hexadecyl, 8,8-dimethyldodecyl, 2-tetradecyl groups, and 6-methylundecyl.

Preferred compounds of the present invention are those wherein X is NH and Ar is phenyl or substituted phenyl with substituted phenyl being more preferred. The most preferred compounds of this invention are those wherein Ar is phenyl disubstituted on the 2,6-positions or trisubstituted on the 2,4,6-positions and wherein each of $R_5$ and $R_6$ is hydrogen with compounds wherein Ar is 2,6 diisopropylphenyl being especially preferred.

Pharmaceutical compositions containing the compounds of Formula I and methods of using the compounds of Formula I to lower blood cholesterol levels are also included in the scope of the present invention.

As shown by the data presented below in Table 1, the compounds of the present invention are potent inhibitors of the enzyme acyl-CoA:cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia or atherosclerosis.

The ability of representative compounds of the present invention to inhibit ACAT was measured using an in vitro test more fully described in F. J. Field and R. G. Salone, Biochemica et Biophysica 712:557–570 (1982). The test assesses the ability of a test compound to inhibit the acylation of cholesterol by oleic acid by measuring the amount of radiolabeled cholesterol oleate formed from radiolabeled oleic acid in a tissue preparation containing rabbit intestinal microsomes.

The data appear in Table 1 where they are expressed as $IC_{50}$ values; i.e., the concentration of test compound required to inhibit the activity of the enzyme by 50%.

TABLE 1

| Example | IAl $IC_{50}$ ($\mu$M) |
| --- | --- |
| 1 | 1.02 |
| 2 | 0.83 |
| 3 | >5 |
| 4 | 0.51 |
| 5 | >5 |
| 6 | 1.19 |
| 7 | 1.27 |
| 8 | 13 |
| 10 | 5.0 |
| 11 | 0.086 |
| 14 | 2.0 |
| 15 | 9.2 |

In one in vivo screen designated APCC, male Sprague-Dawley rats (200 to 225 g) were randomly divided into treatment groups and dosed at 4 PM with either vehicle (CMC/Tween) or suspensions of compounds in vehicle. The normal chow diet was then replaced with a high fat, high cholesterol diet with 0.5% cholic acid. The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention appear in Table 2. The compounds were dosed at 30 mg/kg unless otherwise noted.

TABLE 2

| Example | APCC (% ΔTC) |
|---|---|
| 1 | −76 |
| 2 | −56 |
| 3 | −34 |
| 6 | −63 |
| 7 | −64 |
| 8 | −31 |
| 10 | −14 |
| 11 | −49 |
| 14 | −72 |
| 15 | −75 |

In therapeutic use as agents for treating hypercholesterolemia or atherosclerosis, the compounds of Formula I or pharmaceutically acceptable salts thereof are administered to the patient at dosage levels of from 250 to 3000 mg per day. For a normal human adult of approximately 70 kg of body weight, this translates into a dosage of from 5 to 40 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without carriers) is surrounded by a carrier, which is thus in association with it. In a similar manner cachets are also included.

Tablets, powders, cachets, and capsules can be used as solid dosage forms suitable for oral administration.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The compounds of the present invention can be prepared by various means. Overall, the means by which the compounds of Formula I are prepared is set forth in Chart I hereof. In Chart I X, $R_2$ and Ar have the meanings defined in Formula I, and $R_8$ is lower alkyl having from 1 to 4 carbon atoms or benzyl. Typically, the sulfonyl chloride (1) is reacted with ammonium hydroxide in methanol or ethanol to give the sulfonamide (2). The sulfonamide (2) is reacted with an appropriate arylisocyanate, (ArNCO) or aryl chloroformate (ArO-COCl), in dimethylformamide and sodium hydride to give the sulfonyl urea (3) or sulfonyl carbamate (5), respectively, which can be alkylated using an appropriate benzyl halide or alkylhalide, $R_8$halo, wherein $R_8$ is benzyl or lower alkyl$C_{1-4}$ and halo is chlorine, bromine, or iodine in acetonitrile and 1,8-diazabicyclo[5.4.0]undec-7-ene to give compounds (4) and (6). The base salts of the sulfonyl ureas (3) or the sulfonyl carbamates (5) are formed by reacting these compounds with an appropriate base.

The sulfonyl chlorides (1) are commercially available or can be prepared by well known procedures as generally outlined in Chart II hereof in Scheme I.

In Scheme I, X is chlorine, bromine, or iodine, and $R_9$ is typically a straight chain alkyl group having from 5 to 17 carbon atoms. The aliphatic halide, $R_9X$, is reacted with sodium sulfonite in aqueous ethanol at reflux to give the aliphatic sodium sulfonate, $R_9SO_3Na$, which is treated with phosphorous oxychloride or phosphorous pentachloride to give the sulfonyl chloride derivative $R_9SO_2Cl$.

In Scheme II of Chart II there is set forth a means for obtaining the sulfonamides (2) of Chart I. In Scheme II $R_{10}$ and $R_{11}$ can be hydrogen, methyl, ethyl, or phenyl or $R_{10}$ and $R_{11}$ can be taken together with the carbon to which they are attached to form a cycloalkyl group having from 3 to 8 carbon atoms and R can be a straight or branched alkyl group having from 4 to 16 carbon atoms. The sulfonyl chloride (a) is treated with t-butylamine in tetrahydrofuran to give the N-t-butylsulfonamide derivative (b) which is treated with two equivalents of n-butyllithium according to the procedure set forth in J. Org. Chem. 49:1700–1703 (1984), followed by treatment with an alkylating agent RX wherein R is as defined above and X is bromine or iodine to give compounds (c) which are treated with trifluoroacetic acid to give the sulfonamides (d).

The following specific examples will further illustrate the synthesis of compounds of the present invention.

EXAMPLE 1

N-[2,6-Bis(1-methylethyl)phenyl]-N'-(2-pentadecylsulfonyl)urea (a) n-BuLi (1.6M, 32 mL) was added dropwise to a 0° C. solution of N-t-butylethanesulfonamide (4.0 g, 24 mmoles) in anhydrous THF (80 mL) under dry $N_2$. The solution was stirred for 30 minutes at 0° C then warmed to room temperature for 30 minutes. It was then cooled back to 0° C. and a solution of 1-bromotridecane (6.4 mL, 25 mmoles) in 10 mL anhydrous THF (distilled from Na-Ph$_2$CO) was added dropwise. The solution was allowed to warm to room temperature overnight, quenched by addition of 1N HCl (60 mL), and partitioned between ethyl acetate and brine. The organic layer was dried, filtered, and concentrated to an oil, which was dissolved in 40 mL of CF$_3$CO$_2$H and stirred overnight at room temperature. It was then concentrated and the solid residue recrystallized from iPr$_2$O to afford 4.8 g (68%) of 2-pentadecylsulfonamide as a light brown (almond) powder.

(b) A solution of 2-pentadecylsulfonamide (2.91 g, 10 mmoles) in DMF (40 mL dried over 3 Å sieves) was added dropwise to a stirred, 0° C. suspension of NaH (0.5 g, 21 mmoles of hexane washed) in 10 mL dry DMF. The mixture was stirred 30 minutes at 0° C., then warmed to room temperature for 3 hours. It was then cooled back to 0° C. and a solution of 2,6-diisopropylphenylisocyanate (2.14 mL, 10 mmoles) in 10 mL DMF was added dropwise. The mixture was allowed to warm to room temperature overnight, cooled to 0° C., and quenched by dropwise addition of 1N HCl (60 mL). The mixture was partitioned between EtOAc (300 mL) and H$_2$O (100 mL). The organic layer was further washed with brine, dried, filtered, and evaporated to provide an oil which was flash chromatographed (silica gel, 4:1 hexane-EtOAc) to produce 3 g of an oil which solidified on standing (m.p. 65°–75° C.).

EXAMPLE 2

N-[2,6-Bis(1-methylethyl)phenyl]-N'-(tetradecylsulfonyl)urea (a) Sodium, 1-tetradecane sulfonate A mixture of 1-bromotetradecane (59.5 g, 200 mmoles) and Na$_2$SO$_3$ (27.86 g, 221 mmoles) was stirred and heated in 200 mL of 1:1 H$_2$O—EtOH at reflux while stirring vigorously. The mixture was refluxed overnight, cooled to 0° C., and the precipitate isolated by suction filtration and dried at 70° C. under vacuo. Isolated 22.2 g of colorless solid, m.p. >235° C.

(b) 1-Tetradecanesulfonamide

A mixture of POCl$_3$ (19 mL, ~200 mmoles) and sodium, 1-tetradecanesulfonate (34.8 g, 115 mmoles) was stirred and heated at 180° C. for 18 hours. After cooling to room temperature, the mixture was digested with ice water, then partitioned between EtOAc and water (500 mL each). The aqueous layer was further extracted with EtOAc. The combined EtOAc extracts were washed with brine (200 mL), dried, filtered, and evaporated. The residue was combined with 200 mL concentrated NH$_4$OH and heated on a steam bath until gas evolution was complete (~30 minutes) with swirling. The mixture was then concentrated and partitioned between ethyl acetate (EtOAc) and water. The aqueous layer was exhaustively extracted with EtOAc. The EtOAc extracts were washed with brine and dried. Recrystallization of the solid which remained after filtration and concentration from EtOAc afforded 10.4 g of 1-tetradecylsulfonamide, m.p. 92°–93° C.

(c) A solution of 1-tetradecylsulfonamide (9.0 g, 32.4 mmoles) in DMF (90 mL) was added dropwise to a stirred suspension of NaH (1.63 g, 68 mmoles) in 30 mL of DMF. The solution was stirred 60 minutes, then 2,6-diisopropylphenyl isocyanate (7.0 mL, 33 mmoles) was added dropwise. The mixture was stirred overnight at room temperature, then quenched by dropwise addition of 1M HCl. The mixture was then partitioned between H$_2$O and ethyl acetate (500 mL each). The aqueous layer was further extracted with ethyl acetate. The combined ethyl acetate extracts were diluted with hexane (100 mL) and then washed exhaustively with H$_2$O. The organic extracts were dried, filtered, and concentrated to a solid residue, which was triturated with ether and the solid isolated by suction filtration and dried. Isolated 9.70 g of solid, m.p. 135°–137° C.

EXAMPLE 3

N-[2,6-Bis(1-methylethyl)phenyl]-N'-methyl-N'-(tetradecylsulfonyl)urea

CH$_3$I (0.15 mL, 2 3 mmoles) was added dropwise to a room temperature solution of N-[2,6-bis(1-methylethyl)phenyl]-N'-(tetradecylsulfonyl)urea (1.0 g, 2.08 mmoles) and 1,8-diazabicyclo[5.4.0]undec-7-ene (0 34 mL, 2.3 mmoles), stirring in 10 mL of CH$_3$CN. The solution was stirred overnight at room temperature, diluted with EtOAc, washed with 1M HCl, H$_2$O, brine, and dried (MgSO$_4$). Filtration and evaporation afforded an oil which was flash chromatographed (silica gel, 10:1 hexane-ethyl acetate) to provide 800 mg of a colorless oil.

Anal. Calcd. for C$_{28}$H$_{50}$N$_2$O$_3$S:
C, 67.97; H, 10.19; N, 5.66; S, 6.48.
Found: C, 68.58; H, 10.21; N, 5.83; S, 6.14.

EXAMPLE 4

N-[2,6-Bis(1-methylethyl)phenyl]-N'-phenylmethyl-N'-tetradecylsulfonyl)urea

Benzyl bromide (0.2 mL, 1.68 mmoles) was added to a stirred, room temperature solution of N-[2,6-bis(1-methylethyl)phenyl]-N'-(tetradecylsulfonyl)urea (0.5 g, 1 mmole) and DBU (0.16 mL, 1 1 mmoles) in 10 mL of CH$_3$CN. The mixture was allowed to stir overnight at room temperature, poured into ether (200 mL), and washed with H$_2$O (50 mL), 1N HCl (50 mL), brine (50 mL), and dried (MgSO$_4$). The residue that remained after filtration and concentration was flash chromatographed on silica gel (25:1 v/v, hexane-ethyl acetate) to afford 300 mg of an oil which solidified on standing, m.p. 50°–53° C.

When in the procedure of Example 2, step (a) an appropriate amount of 1-bromooctane, 1-bromododecane, 1-bromohexadecane, 1-bromodecane, or 1-bromotridecane is substituted for 1-bromotetradecane and the general procedure of step (a) is followed, the following salts were obtained:
sodium, 1-octane sulfonate,
sodium, 1-dodecane sulfonate,
sodium 1-hexadecane sulfonate,
sodium, 1-decane sulfonate, and
sodium, 1-tridecane sulfonate.

When in the procedure of Example 2, step (b) each of the above-obtained salts is substituted for sodium, 1-tetradecane sulfonate and the general procedure of step (b) is followed, the following respective compounds were obtained:
1-octanesulfonamide,
1-dodecanesulfonamide,
1-hexadecanesulfonamide,
1-decanesulfonamide, and
1-tridecanesulfonamide.

When in the procedure of Example 2, step (c) each of the above obtained sulfonamides is substituted for 1-tetradecanesulfonamide and the general procedure of step (c) is followed, the following respective products (Examples 6-9) were obtained:

EXAMPLE 5

N-[2,6-Bis(1-methylethyl)phenyl]-N'-(octylsulfonyl)urea, m.p. 133°-136° C.

EXAMPLE 6

N-[2,6-Bis(1-methylethyl)phenyl]-N'-(dodecylsulfonyl)urea, m.p. 125°-127° C.

EXAMPLE 7

N-[2,6-Bis(1-methylethyl)phenyl]-N'-(hexadecylsulfonyl)urea, m.p. 123°-126° C.

EXAMPLE 8

N-[2,6-Bis(1-methylethyl)phenyl]-N'-(decylsulfonyl)urea, m.p. 152°-154° C.

EXAMPLE 9

N-[2,6-Bis(1-methylethyl)phenyl]-N'-(tridecylsulfonyl)urea, m.p. 121°-123° C.

EXAMPLE 10

N-(2,4-Difluorophenyl)-N'-(tetradecylsulfonyl)urea

When in the procedure of Example 2, part (c) an appropriate amount of 2,6 difluorophenyl isocyanate is substituted for 2,6-diisopropylphenyl isocyanate and the general procedure of part (c) is followed, the title compound is obtained, m.p. 88°-92° C.

EXAMPLE 11

N-[2,6-Bis(1-methylethyl)phenyl]-N'-methyl-N'-dodecylsulfonyl)urea

When in the procedure of Example 3 an appropriate amount of the product of Example 7 was substituted for N-[2,6-bis(1-methylethyl)phenyl]-N'-(tetradecylsulfonyl)urea and the procedure of Example 3 was followed, the title compound was obtained as an oil.

EXAMPLE 12

N-(2,4,6-Trimethoxyphenyl)-N'-(hexadecylsulfonyl)urea

When in the procedure of Example 2, part (c) an appropriate amount of 1-hexadecanesulfonamide is substituted for 1-tetradecanesulfonamide, and an appropriate amount of 2,4,6-trimethoxyphenylisocyanate is substituted for 2,6-diisopropylphenylisocyanate and the general procedure of Example 2, part (c) is followed, the title compound was obtained.

EXAMPLE 13

N-[2,6-Bis(1-methylethyl)phenyl]-N'-(2-methyl-2-pentadecylsulfonyl)urea

When in the procedure of Example 1 (a) an appropriate amount of N-t-butyl isopropylsulfonamide was substituted for N-t-butyl ethanesulfonamide and the general procedure of Example 1(a) was followed, 2-methyl-2-pentadecylsulfonamide was obtained, and when an appropriate amount of said sulfonamide was substituted for 2-pentadecylsulfonamide in the procedure of Example 1(b) and the general procedure of Example 1(b) was followed, the title compound was obtained.

EXAMPLE 14

N-[2,6-Bis(1-methylethyl)phenyl]-N'-(1-phenyl-1-tetradecylsulfonyl)urea

When in the procedure of Example 1(a) an appropriate amount of N-t-butyl benzylsulfonamide is substituted for N-t-butylethanesulfonamide and the general procedure of Example 1(a) and 1(b) was followed, the title compound was obtained, m.p. 97°-102° C.

EXAMPLE 15

N-[2,6-Bis(1-methylethyl)phenyl]-N'-(1-phenyl-1-nonylsulfonyl)urea

When in the procedure of Example 1(a) an appropriate amount of N-t-butyl benzylsulfonamide was substituted for N-t-butylethanesulfonamide and an appropriate amount of 1-bromononane was substituted for 1-bromotridecane and the general procedure of Example 1(a) and 1(b) was followed, the title compound was obtained, m.p. 145°-146° C.

EXAMPLE 16

N-2,6-Bis(1-methylethyl)phenyl]-N'-(2-decylsulfonyl)urea

When in the procedure of Example 1(a) an appropriate amount of 1-bromooctane was substituted for 1-bromotridecane and the general procedure of Example 1(a) and 1(b) was followed, the title compound was obtained, CI MS M+ 424.

EXAMPLE 17

2,6-Bis(1-methylethyl)phenyl]-N'-(tetradecylsulfonyl)carbamate

When in the procedure of Example 2, part (c) an appropriate amount of [2,6-bis(1-methylethyl)phenyl]-chloroformate (M. V. Zabik; R. D. Schuetz, J. Org. Chem. 32, 300-7 (1967)) is substituted for 2,6-diisopropylphenyl isocyanate and the general procedure of part (c) is followed, the title compound is obtained.

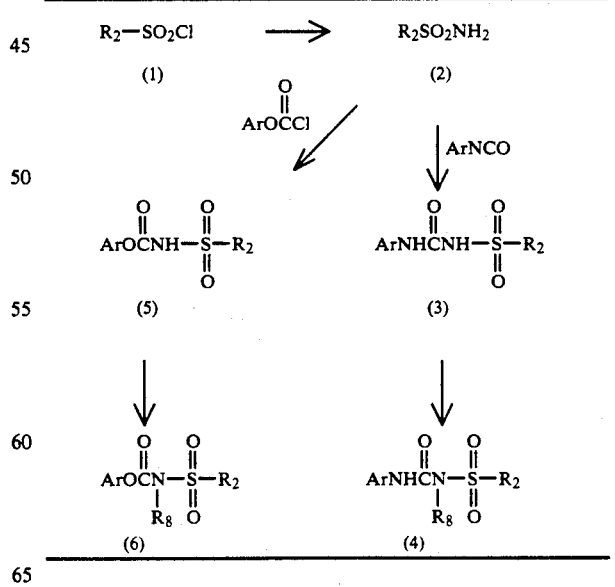

Chart I

Chart II

SCHEME 1

Chart II-continued

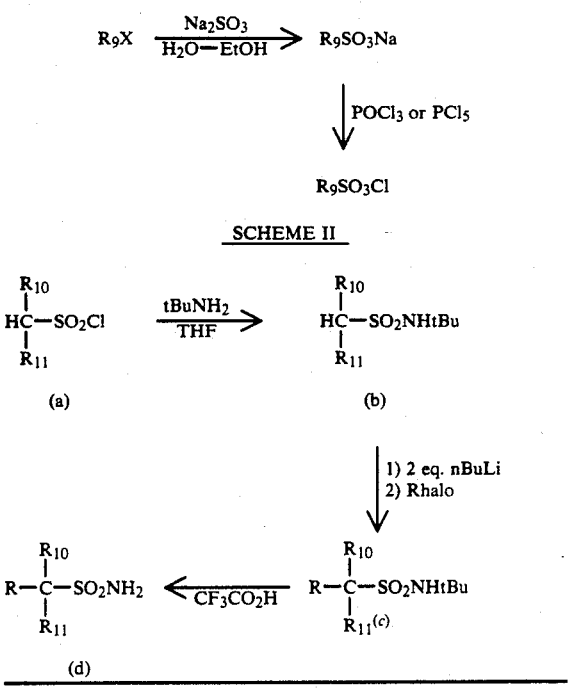

SCHEME II

What is claimed is:

1. A method for treating atherosclerosis in a patient in need thereof which comprises administering to said patient an effective amount of a compound of the formula

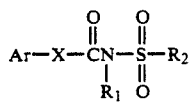

wherein X is —NH—; wherein Ar is
(a) phenyl which is unsubstituted or is substituted with from one to three substituents selected from:
alkyl having from 1 to 4 carbon atoms and which is straight or branched,
alkoxy having from 1 to 3 carbon atoms and which is straight or branched,
hydroxy,
fluorine,
chlorine,
bromine,
nitro,
cyano,
trifluoromethyl,
—COOH,
—COOalkyl wherein alkyl has from 1 to 4 carbon atoms and which is straight or branched,
—$(CH_2)_m NR_3 R_4$ wherein m is zero or one, and each of $R_3$ and $R_4$ is hydrogen or a straight or branched alkyl group having 1 to 4 carbon atoms;
(b) 1- or 2-naphthyl which is unsubstituted or substituted with one to three substituents selected from:
alkyl having from 1 to 4 carbon atoms and which is straight or branched,
alkoxy having from 1 to 3 carbon atoms and which is straight or branched,
hydroxy,
fluorine,
chlorine,
bromine,
nitro,
cyano,
trifluoromethyl,
—COOH,
—COOalkyl wherein alkyl has from 1 to 4 carbon atoms and is straight or branched,
—$(CH_2)_m NR_3 R_4$ wherein m, $R_3$, and $R_4$ have the meanings defined above;
wherein $R_1$ is hydrogen, lower alkyl having from 1 to 4 carbon atoms or benzyl; wherein $R_2$ is

wherein each of $R_5$ and $R_6$ is hydrogen, methyl, ethyl, phenyl, phenyl substituted with straight or branched lower alkyl having from 1 to 4 carbon atoms, straight or branched lower alkoxy having from 1 to 4 carbon atoms, chlorine, fluorine or bromine, or $R_5$ and $R_6$ together with the carbon atom to which they are attached form a cyclic group having from 3 to 8 carbon atoms; and $R_7$ is a straight or branched alkyl group having from 4 to 16 carbon atoms; and pharmaceutically acceptable salts thereof; in combination with a pharmaceutically acceptable carrier.

2. A method for treating atherosclerosis in a patient in a need thereof as defined in claim 1 wherein Ar is phenyl disubstituted on the 2,6-positions of trisubstituted on the 2, 4, 6-positions.

3. A method for treating atherosclerosis in a patient in need thereof as defined in claim 2 wherein Ar is phenyl disubstituted on the 2,6-positions with isopropyl groups or phenyl trisubstituted on the 2-, 4-, 6-positions with methoxy and each of $R_5$ and $R_6$ is hydrogen.

* * * * *

UNITED STATES PATENT AND TRADEMARK OFFICE
CERTIFICATE OF CORRECTION

PATENT NO. : 5,254,589
DATED : Oct. 19, 1993
INVENTOR(S) : Picard et al.

It is certified that error appears in the above-indentified patent and that said Letters Patent is hereby corrected as shown below:

Column 14, line 47, remove "a" before "need".

Column 14, line 48, "of" should read "or".

Signed and Sealed this

Eighteenth Day of October, 1994

*Attest:*

BRUCE LEHMAN

*Attesting Officer*     *Commissioner of Patents and Trademarks*